US012721794B2

(12) United States Patent
Lee et al.

(10) Patent No.: US 12,721,794 B2
(45) Date of Patent: Sep. 1, 2026

(54) COSMETIC COMPOSITION OF LIQUID CRYSTAL LIPID PARTICLES FOR HAIR CARE COMPOSITION

(71) Applicant: BASF SE, Ludwigshafen (DE)

(72) Inventors: Dong Ryeol Lee, Shanghai (CN); Zhao Ting Liu, Shanghai (CN); Yang Zhang, Shanghai (CN)

(73) Assignee: BASF SE, Ludwigshafen am Rhein (DE)

( * ) Notice: Subject to any disclaimer, the term of this patent is extended or adjusted under 35 U.S.C. 154(b) by 1004 days.

(21) Appl. No.: 17/617,061

(22) PCT Filed: Jul. 8, 2020

(86) PCT No.: PCT/EP2020/069239
§ 371 (c)(1),
(2) Date: Dec. 7, 2021

(87) PCT Pub. No.: WO2021/005104
PCT Pub. Date: Jan. 14, 2021

(65) Prior Publication Data

US 2022/0323317 A1 Oct. 13, 2022

(30) Foreign Application Priority Data

Jul. 11, 2019 (WO) ................ PCT/CN2019/095622

(51) Int. Cl.

| | |
|---|---|
| ***A61K 8/14*** | (2006.01) |
| ***A61K 8/02*** | (2006.01) |
| ***A61K 8/34*** | (2006.01) |
| ***A61K 8/39*** | (2006.01) |
| ***A61K 8/44*** | (2006.01) |
| ***A61K 8/60*** | (2006.01) |
| ***A61K 8/92*** | (2006.01) |
| ***A61Q 5/00*** | (2006.01) |

(52) U.S. Cl.
CPC ............. *A61K 8/14* (2013.01); *A61K 8/0295* (2013.01); *A61K 8/345* (2013.01); *A61K 8/39* (2013.01); *A61K 8/447* (2013.01); *A61K 8/608* (2013.01); *A61K 8/92* (2013.01); *A61Q 5/00* (2013.01)

(58) Field of Classification Search
CPC ........ A61K 8/14; A61K 8/0295; A61K 8/345; A61K 8/39; A61K 8/447; A61K 8/608; A61K 8/92; A61Q 5/00
See application file for complete search history.

(56) References Cited

U.S. PATENT DOCUMENTS

| | | | | |
|---|---|---|---|---|
| 2010/0158790 | A1 * | 6/2010 | Jakli | H10F 77/147<br>977/773 |
| 2012/0071568 | A1 * | 3/2012 | Sugiyama | A61K 8/891<br>510/159 |
| 2017/0105909 | A1 | 4/2017 | Miyahara et al. | |
| 2017/0312207 | A1 * | 11/2017 | Saeki | A61P 43/00 |
| 2018/0303727 | A1 * | 10/2018 | Riedel | A61K 8/062 |

FOREIGN PATENT DOCUMENTS

| | | | | |
|---|---|---|---|---|
| DE | 102009034140 | A1 * | 5/2010 | C07C 69/003 |
| EP | 1264632 | A1 * | 12/2002 | C09K 23/017 |
| EP | 2448550 | B1 | 4/2019 | |
| JP | 2018-532781 | A | 11/2018 | |
| KR | 2016-0141367 | A | 12/2016 | |
| KR | 10-2017-0008728 | A | 1/2017 | |
| WO | WO-2018/108530 | A1 | 6/2018 | |
| WO | 2018/215136 | A1 | 11/2018 | |

OTHER PUBLICATIONS

Machine translation for EP-1264632-A1 (Year: 2002).*
Machine translation for DE-102009034140-A1 (Year: 2010).*
Madheswaran et al.; "In Vitro and In Vivo Skin Distribution of 5a-Reductase Inhibitors Loaded Into Liquid Crystalline Nanoparticles"; Elsevier; Journal of Pharmaceutical Sciences 106 (2017) 3385-3394 (Year: 2017).*
Google Search; is glyceryl stearate equivalent to glycerol stearate; accessed Jan. 2025 (Year: 2025).*
Google Search; orthorhombic lateral packing; accessed Jan. 2025 (Year: 2025).*
"Carrefour—GS, Italy, Conditioner", Database GNPD [Online], Mintel, retrieved from STN Database accession No. 1118601, Jun. 2009, 3 pages.
"Colgate-Palmolive, Poland, Conditioner", Database GNPD [Online], Mintel, retrieved from STN Database accession No. 5651121, May 2018, 3 pages.
"Lea Nature, France, Apple Softness Shampoo", Database GNPD [Online], Mintel, retrieved from STN Database accession No. 5619073, Apr. 2018, 3 pages.
International Preliminary Report on Patentability received for PCT Patent Application No. PCT/EP2020/069239, mailed on Jan. 20, 2022, 11 pages.
"Body Foam", Database GNPD [Online], Mintel, retrieved from Database accession No. 5805731, XP055730748, Jul. 4, 2018, 3 pages.
"Neue Emulgatoren f. ur kosmetische AP/Deo Zubereitungen", Research Disclosure, Kenneth Mason Publication, vol. 491, Issue 26, Mar. 1, 2005, 2 pages.
"Reduced textile staining by use of cosmetic AP/Deo formulations ED—Darl Kuhn", ip.com, ip.com Inc., West Henrietta, NY, US,Dec. 2, 2013.

(Continued)

*Primary Examiner* — Robert A Wax
*Assistant Examiner* — John W Lippert, III
(74) *Attorney, Agent, or Firm* — Faegre Drinker Biddle & Reath LLP

(57) ABSTRACT

The presently claimed invention relates to liquid crystal lipid particles. The presently claimed invention relates to liquid crystal lipid particles which are used in hair care composition and exhibit excellent hair moisturizing effect.

26 Claims, No Drawings

(56) References Cited

OTHER PUBLICATIONS

International Application No. PCT/EP2020/069239, International Search Report and Written Opinion, mailed Oct. 7, 2020.
Mitchell, et al., “Phase behaviour of polyoxyethylene surfactants with water. Mesophase structures and partial miscibility (cloud points)”, Journal of the Chemical Society, Faraday Transactions 1: Physical Chemistry in Condensed Phases, vol. 79, Issue 4, 1983, pp. 975-1000.

* cited by examiner

COSMETIC COMPOSITION OF LIQUID CRYSTAL LIPID PARTICLES FOR HAIR CARE COMPOSITION

CROSS-REFERENCE TO RELATED APPLICATIONS

This is the U.S. national phase of International Application No. PCT/EP2020/069239, filed Jul. 8, 2020, which claims the benefit of International Patent Application No. PCT/CN2019/095622, filed on Jul. 11, 2019.

FIELD OF INVENTION

The presently claimed invention relates to liquid crystal lipid particles. In particular, the presently claimed invention relates to liquid crystal lipid particles which are used in hair care compositions. The hair care compositions containing the liquid crystal lipid composition has a good conditioning effect on the hair.

BACKGROUND

Hair is subjected to a wide variety of severe stress, because of environmental influences, such as UV irradiation or weathering, mechanical stresses, such as combing, or various hair treatments, such as washing, drying with hot air, bleaching, coloring, perming, etc., which can lead to hair damage. Damage of hair includes e.g. dryness, reduced elasticity, brittleness, split ends, dullness, matte appearance, reduced fullness, rough surface and reduced mechanical strength. This leads to impaired combability, reduced shine, increased electrostatic charging and a tendency to break.

Therefore, there is a need for hair cosmetic compositions with a complex profile of properties which counteract the negative effects of stressed hair in as diverse a manner as possible. The hair cosmetic compositions should be characterized by good conditioning, care, protective and hair-damage repairing properties. It is also important that the components used could be easily formulated and have a high compatibility. Moreover, the finished products should have good application properties.

Furthermore, silicone oils and/or hair polymers containing silicone groups are often used in conditioning hair cosmetic compositions. The desired effects from using silicone are the generation of shine, improvement in the combability or the enclosure of split ends or other kind of hair damage. However, due to various reasons, the use of silicones in hair conditioner is undesired. For example, hair damage is often merely concealed by silicone-containing conditioners and not permanently repaired. The actual condition of the hair under the silicone is no longer evident, and targeted compensating care becomes difficult. Water-insoluble silicones tend to "build-up" on the hair, and the hair becomes heavy and lifeless. Under the silicone layer, the hair can dry out unnoticed, which can lead to increased split ends and hair breakage.

Moreover, silicone or silicone oil is considered harmful to the environment and, thus, it is essential that environmentally friendly alternatives be explored.

Thus, alternatives for conditioning hair cosmetic compositions are explored, whereby the use of silicone compounds can be reduced or avoided.

Accordingly, there is a need for a hair conditioning composition which has good conditioning properties that are comparably effective to conditioners based on silicone compounds known from the prior art.

SUMMARY OF THE INVENTION

Surprisingly, it was found that the liquid crystal lipid particles of the presently claimed invention are effective in improving the hair conditioning effect and were found to be comparably effective to silicone as a hair conditioner.

Liquid crystal lipid particles are a type of system which offers the dual advantage of a liquid phase and solid phase. These particles can be easily manufactured and offer several advantages.

Hence, in one aspect, the presently claimed invention relates to a method for conditioning of hair comprising applying to the hair at least one liquid crystal lipid particle, wherein the liquid crystal lipid particle comprises, at least one compound of formula (I)

general formula (I)

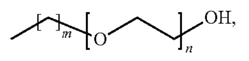

wherein m is an integer in the range from ≥10 to ≤24 and n is an integer in the range from ≥1 to ≤25, at least one compound of formula (II)

general formula (II)

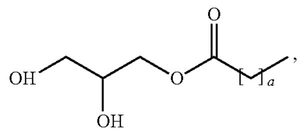

wherein a is an integer in the range from ≥10 to ≤24, at least one compound of formula (III)

general formula (III)

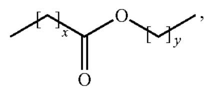

wherein x is an integer in the range from ≥10 to ≤24 and y is an integer in the range from ≥10 to ≤25, at least one compound of formula (IV)

general formula (IV)

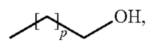

wherein p is an integer in the range from ≥10 to ≤16, at least one compound of formula (V)

general formula (V)

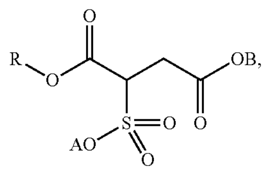

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

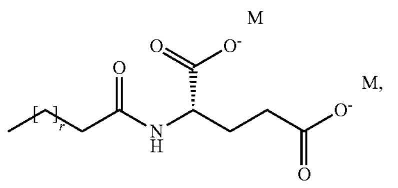

wherein r is an integer in the range from ≥9 to ≤18, and M is a hydrogen atom, an alkali earth metal or an alkaline earth metal.

In yet another aspect, the present invention relates to the use of at least one liquid crystal lipid particle for conditioning of the hair, wherein the liquid crystal lipid particle comprises at least one compound of formula (I)

general formula (I)

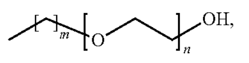

wherein m is an integer in the range from ≥10 to ≤24 and n is an integer in the range from ≥1 to ≤25, at least one compound of formula (II)

general formula (II)

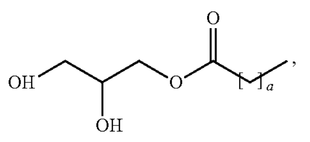

wherein a is an integer in the range from ≥10 to ≤24, at least one compound of formula (III)

general formula (III)

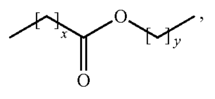

wherein x is an integer in the range from ≥10 to ≤24 and y is an integer in the range from ≥10 to ≤25, at least one compound of formula (IV)

general formula (IV)

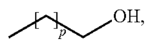

wherein p is an integer in the range from ≥10 to ≤16, at least one compound of formula (V)

general formula (V)

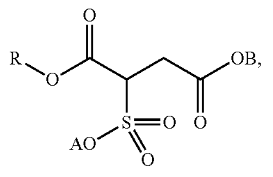

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

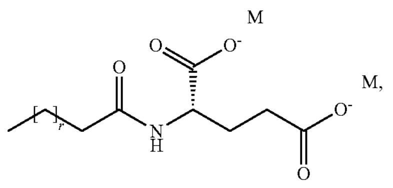

wherein r is an integer in the range from ≥9 to ≤18, and M is a hydrogen atom, an alkali earth metal or an alkaline earth metal In a further aspect, the present invention relates to a hair care composition that comprises at least one liquid crystal particle as described above, at least one cosmetically acceptable additive and water.

Another aspect of the presently claimed invention relates to the use of the hair care composition as described herein above and below or the at least one liquid crystal lipid particle as described herein above and below for the conditioning of hair.

DETAILED DESCRIPTION OF THE INVENTION

Before the present compositions and formulations of the presently claimed invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms ‘first’, ‘second’, ‘third’ or ‘a’, ‘b’, ‘c’, etc. and the like in the description and in the claims, are used for distinguishing between similar elements and not necessarily for describing a sequential or chronological order. It is to be understood that the terms so used are interchangeable under appropriate circumstances and that the embodiments of the presently claimed invention described herein are capable of operation in other sequences than described or illustrated herein. In case the terms ‘first’, ‘second’, ‘third’ or ‘(A)’, ‘(B)’ and ‘(C)’ or ‘(a)’, ‘(b)’, ‘(c)’, ‘(d)’, ‘i’, ‘ii’ etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

Furthermore, the ranges defined throughout the specification include the end values as well i.e. a range of 1 to 10 implies that both 1 and 10 are included in the range. For the avoidance of doubt, applicant shall be entitled to any equivalents according to applicable law. In the following passages, different aspects of the presently claimed invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to 'one embodiment' or 'an embodiment' means that a particular feature, structure or characteristic described in connection with the embodiment is included in at least one embodiment of the presently claimed invention. Thus, appearances of the phrases 'in one embodiment' or 'in an embodiment' in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the presently claimed invention, and form different embodiments, as would be understood by those in the art. For example, in the appended claims, any of the claimed embodiments can be used in any combination "Hair care" as used herein includes protecting the hair in various conditions which lead to hair damage which includes environmental influences, such as UV irradiation or weathering, mechanical stresses, such as combing, or various hair treatments, such as washing, drying with hot air, bleaching, coloring, perming.

"Cosmetically acceptable additive" as used herein includes that additive which are generally acceptable for use in cosmetics formulations and provides specific functions.

"Liquid crystal lipid particle" as defined herein comprises lamellar liquid crystal phase with orthorhombic lateral packing.

The presently claimed invention relates to a method for conditioning of hair, comprising applying to the hair at least one liquid crystal lipid particle, wherein the liquid crystal lipid particle comprises, at least one compound of formula (I)

general formula (I)

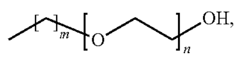

wherein m is an integer in the range from ≥10 to ≤24 and n is an integer in the range from ≥1 to ≤25, at least one compound of formula (II)

general formula (II)

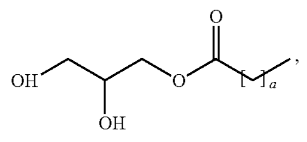

wherein a is an integer in the range from ≥10 to ≤24, at least one compound of formula (III)

general formula (III)

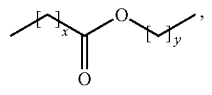

wherein x is an integer in the range from ≥10 to ≤24 and y is an integer in the range from ≥10 to ≤25, at least one compound of formula (IV)

general formula (IV)

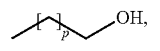

wherein p is an integer in the range from ≥10 to ≤16, at least one compound of formula (V)

general formula (V)

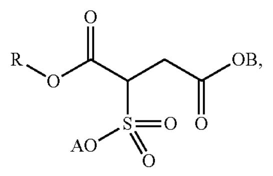

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

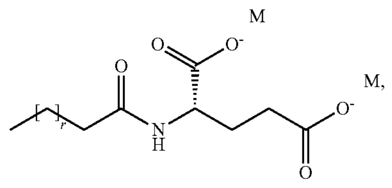

wherein r is an integer in the range from ≥9 to ≤18, and M is a hydrogen atom, an alkali earth metal or an alkaline earth metal.

In an embodiment, the presently claimed invention is directed to the use of at least one liquid crystal lipid particle for conditioning of the hair, wherein the liquid crystal lipid particle comprises, at least one compound of formula (I)

general formula (I)

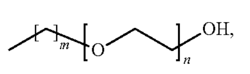

wherein m is an integer in the range from ≥10 to ≤24 and n is an integer in the range from ≤1 to 25, at least one compound of formula (II)

general formula (II)

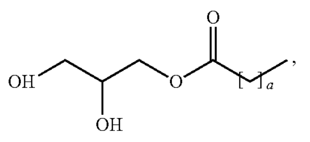

wherein a is an integer in the range from ≥10 to ≤24, at least one compound of formula (III)

general formula (III)

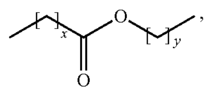

wherein x is an integer in the range from ≥10 to ≤24 and y is an integer in the range from ≥10 to ≤25, at least one compound of formula (IV)

general formula (IV)

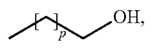

wherein p is an in the range from ≥10 to ≤16, at least one compound of formula (V)

general formula (V)

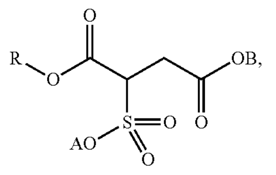

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

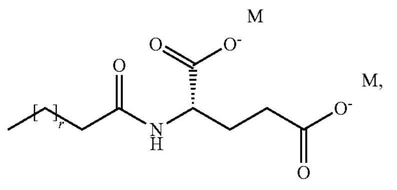

wherein r is an integer in the range from ≥9 to ≤18, and M is a hydrogen atom, an alkali earth metal or an alkaline earth metal In an embodiment of the present invention, the hair care composition comprises at least one liquid crystal particle as described above, at least one cosmetically acceptable additive and water.

In an embodiment of the presently claimed invention, the liquid crystal lipid particles of the presently claimed invention comprise at least one compound selected from the group consisting of compounds represented by the general formulae (I) to (IV), general formula (I)

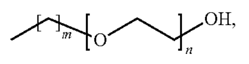

wherein m is an integer in the range from ≥10 to ≤24 and n is an integer in the range from ≥1 to ≤25, general formula (II)

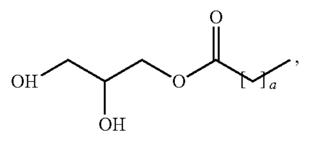

wherein a is an integer in the range from ≥10 to ≤24, general formula (III)

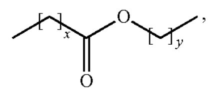

wherein x is an integer in the range from ≥10 to ≤24 and y is an integer in the range from ≥10 to ≤25, and general formula (IV)

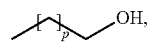

wherein p is an integer in the range from ≥10 to ≤16.

The liquid crystal particles of the presently claimed invention comprise at least one compound selected from the group consisting of compounds represented by the general formula (I) to (IV) and, in addition, at least one compound of general formula (V) or (VI)

general formula (V)

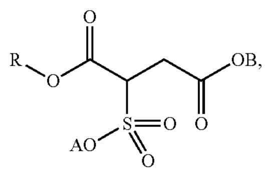

wherein A and B are each independently a hydrogen atom or alkali earth metal or an alkaline earth metal, and R is a linear or branched, saturated or unsaturated $C_{10}$-$C_{20}$ aliphatic radical, general formula (VI)

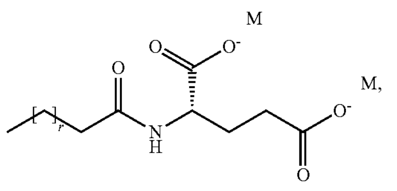

wherein r is an integer in the range from ≥9 to ≤18, and

M is a hydrogen atom, an alkali earth metal or an alkaline earth metal.

In an embodiment of the presently claimed invention, the liquid crystal lipid particles comprise at least one compound represented by the general formula (I) and at least one compound selected from the group consisting of compounds represented by the general formulae (II), (III) and (IV).

In an embodiment of the presently claimed invention, the liquid crystal lipid particles comprise at least one compound represented by the general formula (I) and at least one compound selected from the group consisting of compounds represented by the general formulae (II), (III) (IV), (V), and (VI).

In yet another embodiment of the presently claimed invention, the liquid crystal lipid particles comprise at least one compound represented by the general formula (II) and at least one compound selected from the group consisting of compounds represented by the general formulae (I), (III) and (IV).

In yet another embodiment of the presently claimed invention, the liquid crystal lipid particles comprise at least one compound represented by the general formula (II) and at least one compound selected from the group consisting of compounds represented by the general formulae (I), (III), (IV), (V) and (VI).

In yet another embodiment of the presently claimed invention, the liquid crystal lipid particles comprise at least one compound represented by the general formula (III) and at least one compound selected from the group consisting of compounds represented by the general formulae (I), (II) and (IV).

In yet another embodiment of the presently claimed invention, the liquid crystal lipid particles comprise at least one compound represented by the general formula (III) and at least one compound selected from the group consisting of compounds represented by the general formulae (I), (II), (IV), (V) and (VI).

In yet another embodiment of the presently claimed invention, the liquid crystal lipid particles comprise at least one compound represented by the general formula (IV) and at least one compound selected from the group consisting of compounds represented by the general formulae (I), (II), (III), (V) and (VI).

In a further embodiment of the presently claimed invention, the liquid crystal lipid particles comprise at least one compound represented by the general formula (I) and at least one compound represented by the general formula (II) and at least one compound represented by the general formula (III) and at least one compound represented by the general formula (IV).

In another embodiment of the presently claimed invention, the liquid crystal lipid particles comprise at least one compound represented by the general formula (I) and at least one compound represented by the general formula (II) and at least one compound represented by the general formula (III) and at least one compound represented by the general formula (IV) and at least one compound represented by the general formula (V).

In a further embodiment of the presently claimed invention, the liquid crystal lipid particles comprise at least one compound represented by the general formula (I) and at least one compound represented by the general formula (II) and at least one compound represented by the general formula (III) and at least one compound represented by the general formula (IV) and at least one compound represented by the general formula (VI).

In a further embodiment of the presently claimed invention, the liquid crystal lipid particles comprise at least one compound represented by the general formula (I) and at least one compound represented by the general formula (II) and at least one compound represented by the general formula (III) and at least one compound represented by the general formula (IV) and at least one compound represented by the general formula (VI) and at least one compound represented by the general formula (V), and at least one compound represented by the general formula (VI).

In an embodiment of the presently claimed invention, the liquid crystal lipid particles comprise at least one compound represented by the general formula (I)

general formula (I)

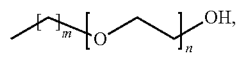

wherein m is an integer in the range from ≥10 to ≤24 and n is an integer in the range from ≥1 to ≤25.

In an embodiment of the presently claimed invention, the at least one compound of the general formula (I) is selected from the group consisting of ceteareths, polyoxyethylene stearyl ether, and polyoxyethylene cetyl ether.

In an embodiment of the presently claimed invention, the at least one compound of general formula (I) is selected from the group consisting of ceteareths-12, ceteareths-20, ceteareths-30.

In a most preferred embodiment of the presently claimed invention, the at least one compound of general formula (I) is selected from the group consisting of ceteareths-12, ceteareths-20.

In an embodiment of the presently claimed invention, in the at least one compound of general formula (II,)

general formula (II)

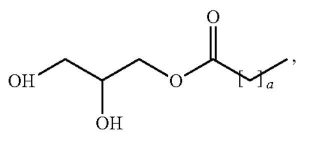

a is an integer in the range from ≥10 to ≤24.

In an embodiment of the presently claimed invention, the at least one compound of general formula (II) is selected from the group consisting of glycerol stearate, glycerol laurate and glycerol palmitate, glycerol caprylate and glycerol myristate.

In a preferred embodiment of the presently claimed invention, the at least one compound of general formula (II) is glycerol stearate.

In an embodiment of the presently claimed invention, in the at least one compound of general formula (III), general formula (III)

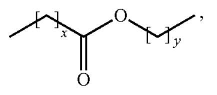

x is an integer in the range from ≥10 to ≤24 and y is an integer in the range from ≥10 to ≤25.

In an embodiment of the presently claimed invention, the at least one compound of general formula (III) is selected from the group consisting of myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate.

In a further embodiment of the presently claimed invention, the at least one compound of general formula (III) is selected from the group consisting of cetyl palmitate, myristyl myristate, tetra decyl tetra decanoate, and behenyl behenate.

In a preferred embodiment of the presently claimed invention, the at least one compound of general formula (III) is selected from the group consisting of cetyl palmitate and myristyl myristate.

In an embodiment of the presently claimed invention, in the at least one compound of general formula (IV), general formula (IV)

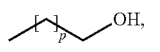

p is an integer in the range from ≥10 to ≤16.

In yet another embodiment of the presently claimed invention, the at least one compound of general formula (IV) is selected from the group consisting of lauryl alcohol, tridecyl alcohol, myristyl alcohol, pentadecyl alcohol, cetyl alcohol, palmitoleyl alcohol, heptadecyl alcohol and stearyl alcohol or mixtures thereof.

In a preferred embodiment of the presently claimed invention, the at least one compound of general formula (IV) is selected from the group consisting of lauryl alcohol, myristyl alcohol, cetyl alcohol and stearyl alcohol or mixtures thereof.

In a most preferred embodiment of the presently claimed invention, the at least one compound of general formula (IV) is a mixture of cetyl alcohol and stearyl alcohol.

In an embodiment of the presently claimed invention, in the at least one compound of general formula (V), general formula (V)

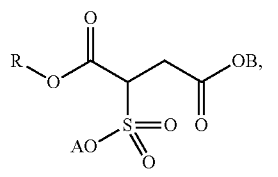

A and B are each independently a hydrogen atom or an alkali earth metal or an alkaline earth metal, and R is a linear or branched, saturated or unsaturated $C_{10}$-$C_{20}$ aliphatic radical.

In an embodiment of the presently claimed invention, in the at least one compound of general formula (V), A and B are each independently an alkali earth metal, and R is a linear or branched, saturated or unsaturated $C_{10}$-$C_{20}$ aliphatic radical.

In a further embodiment of the presently claimed invention, in the at least one compound of general formula (V), R is selected from the group consisting of n-decyl, iso-decyl, n-undecyl, iso-undecyl, n-dodecyl, iso-dodecyl, n-tridecyl, iso-tridecyl, n-tetradecyl, iso-tetradecyl, n-pentadecyl, iso-pentadecyl, n-hexadecyl, iso-hexadecyl, n-heptadecyl, iso-heptadecyl, n-octadecyl, iso-octadecyl and n-octadecenyl.

In a further embodiment of the presently claimed invention, the at least one compound of general formula (V) is disodium $C_{10}$-$C_{18}$ alkyl sulfosuccinate.

In a preferred embodiment of the presently claimed invention, the at least one compound of general formula (V) is disodium $C_{12}$-$C_{18}$ alkyl sulfosuccinate.

In a most preferred embodiment of the presently claimed invention, the at least one compound of general formula (V) is $C_{16}$-$C_{18}$alkyl sulfosuccinate.

In an embodiment of the presently claimed invention, in the at least one compound of general formula (VI), general formula (VI)

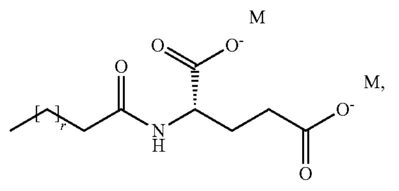

r is an integer in the range from ≥9 to ≤18, and M is a hydrogen atom, an alkali earth metal or an alkaline earth metal.

In an embodiment of the presently claimed invention, in the at least one compound of general formula (VI), M is sodium or potassium and r is an integer in the range from 9 to 18.

In an embodiment of the presently claimed invention, the at least one compound of general formula (VI) is selected from the group consisting of sodium steraroyl glutamate, sodium lauroyl glutamate, sodium cocoyl glutamate, sodium myristoyl glutamate, potassium cocoyl glutamate, and potassium lauroyl glutamate, and combinations thereof.

In an embodiment of the presently claimed invention, the at least one compound of general formula (VI) is selected from the group consisting of sodium lauroyl glutamate, sodium cocoyl glutamate, sodium myristoyl glutamate and sodium steraroyl glutamate.

In an embodiment of the presently claimed invention the crystal lipid particles comprise ceteareths, glycerol stearate, cetyl palmitate, cetyl alcohol and stearyl alcohol.

In yet another embodiment of the presently claimed invention, the liquid crystal lipid particles comprise ceteareths, glycerol stearate, cetyl palmitate, myristyl myristate, cetyl alcohol and stearyl alcohol.

In a further embodiment of the presently claimed invention, the liquid crystal lipid particles comprise ceteareths, glycerol stearate, cetyl palmitate, myristyl myristate, cetyl alcohol, stearyl alcohol and a compound selected from the group of disodium $C_{10}$-$C_{18}$ alkyl sulfosuccinate and sodium steraroyl glutamate.

In a preferred embodiment of the presently claimed invention, the liquid crystal lipid particles comprise ceteareths-20, ceteareths-12, glycerol stearate, cetyl palmitate, myristyl myristate, cetyl alcohol, stearyl alcohol and a compound selected from the group of disodium $C_{16}$-$C_{18}$ alkyl sulfosuccinate and sodium lauroyl glutamate.

In another preferred embodiment of the presently claimed invention, the liquid crystal lipid particles comprise ceteareths-20, ceteareths-12, glycerol stearate, cetyl palmitate, myristyl myristate, cetyl alcohol, stearyl alcohol and a compound selected from the group of disodium $C_{12}$-$C_{14}$ alkyl sulfosuccinate and sodium lauroyl glutamate.

In yet another preferred embodiment of the presently claimed invention, the liquid crystal lipid particles comprise ceteareths-20, ceteareths-12, glycerol stearate, cetyl palmitate, myristyl myristate, cetyl alcohol, stearyl alcohol and a compound selected from the group of disodium $C_{12}$-$C_{14}$ alkyl sulfosuccinate and sodium steraroyl glutamate.

In a most preferred embodiment of the presently claimed invention, the liquid crystal lipid particles comprise ceteareths-20, ceteareths-12, glycerol stearate, cetyl palmitate, myristyl myristate, cetyl alcohol, stearyl alcohol and a compound selected from the group of disodium $C_{16}$-$C_{18}$ alkyl sulfosuccinate and sodium steraroyl glutamate.

In an embodiment of the presently claimed invention, the liquid crystal lipid particles have an average particle size of ≥20 nm to ≤500 nm, determined using dynamic light scattering using Malvern DLS ZS90.

In an embodiment of the presently claimed invention, the liquid crystal lipid particles have an average particle size of ≥20 nm to ≤300 nm, determined using dynamic light scattering using Malvern DLS ZS90.

In an embodiment of the presently claimed invention, the liquid crystal lipid particles have an average particle size of ≥20 nm to ≤150 nm, determined using dynamic light scattering using Malvern DLS ZS90.

In an embodiment of the presently claimed invention, the liquid crystal lipid particles have an average particle size of 20 nm, 30 nm, 40 nm, 50 nm, 60 nm, 70 nm, 80 nm, 90 nm, 100 nm, 110 nm, 120 nm, 130 nm, 140 nm or 150 nm, determined using dynamic light scattering using Malvern DLS ZS90.

Zeta potential of the liquid crystal lipid particles is a measure of the charge on the surface of the particles and is a measure of the stability of the lipid particles. The higher the zeta potential the higher is the stability of the lipid particles.

In an embodiment of the presently claimed invention, the liquid crystal lipid particles have a zeta potential of more than 20 mV, when measured at 40° C. determined using Zetasizer nano ZS90 (Malvern).

In an embodiment of the presently claimed invention, the liquid crystal lipid particles have a zeta potential of more than 30 mV, when measured at 40° C. determined using Zetasizer nano ZS90(Malvern).

In an embodiment of the presently claimed invention, the liquid crystal lipid particles are prepared by using the phase inversion temperature method. In a further embodiment of the presently claimed invention, the liquid crystal lipid particles are prepared using the phase inversion temperature method as disclosed in D. J. Mitchell et al. Phase behavior of polyoxyethylene surfactants with water. Mesophase structures and partial miscibility (cloud points), J. Chem. Soc. Farayday Trans., 79, 975-1000 (1983) incorporated herein by reference.

In an embodiment of the presently claimed invention, the liquid crystal lipid particles have an orthorhombic lateral packing.

In an embodiment of the presently claimed invention, the liquid crystal lipid particles are included in a hair care composition for application to the hair.

In an embodiment of the presently claimed invention, the liquid crystal lipid particles form the base in any hair care for application to the hair.

In an embodiment of the presently claimed invention, the at least one liquid crystal lipid particle is present in an amount in the range of ≥1% to ≤30% by weight, based on the total weight of the hair care composition. In a further embodiment of the presently claimed invention, the at least one liquid crystal lipid particle is present in an amount in the range of ≥1% to ≤25% by weight, based on the total weight of the hair care composition. In a preferred embodiment of the presently claimed invention, the at least one liquid crystal lipid particle is present in an amount in the range of ≥1% to ≤20% by weight, based on the total weight of the hair care composition. In a most preferred embodiment of the presently claimed invention, the at least one liquid crystal lipid particle is present in an amount in the range of ≥1% to ≤15% by weight, based on the total weight of the hair care composition.

In an embodiment of the presently claimed invention, the hair care composition comprises the at least one liquid crystal lipid particle, at least one cosmetically acceptable additive and water.

In an embodiment of the presently claimed invention, the at least one cosmetically acceptable additive is selected from the group consisting of thickeners, viscosity modifiers, surfactants, emulsifiers, perfumes, preservatives, UV protectants, chelating agents, cleansing agents, wetting agents, hair conditioning agents, flexibility enhancers, split modifiers, humectants, propellants, compressed gases, shine enhancers, neutralizing agents, texturizing agents, waterproofing agents, solubilizers, suspension agents, cosmetically active ingredients, hair polymers, light protection agents, bleaches, gel formers, colorants, tinting agents, tanning agents, dyes, pigments, bodying agents, moisturizers, antioxidants, defoamers, anti-statics, emollients, softeners, anti-dandruff agents, hair growth agents, anti-inflammatory agents, anti-microbial agents, foam stabilizers, rheology modifiers, water softening agents, hydrotropes, and buffers.

In an embodiment of the presently claimed invention, the at least one cosmetically acceptable additive is a surfactant and is selected from the group consisting of anionic surfactants, cationic surfactants, amphoteric surfactants and non-ionic surfactants.

In an embodiment of the presently claimed invention, the anionic surfactant is selected from the group consisting of alkyl sulfates, alkyl ether sulfates, alkylester sulfonates, alkylbenzene sulfonates, primary or secondary alkylsulfonates, alkylglycerol sulfonates, sulfonated polycarboxylic acids, sulfates of alkylglycosides, sulfated alkyl amides, alkylphosphates, the salts of saturated or unsaturated fatty acids, polyoxyalkylene ether acetate, paraffin sulfonates, N-acyl N-alkyltaurates, isethionates, alkylsuccinamates, N-acyl sarcosinates, alkylsulfosuccinates, monoesters or diesters of sulfosuccinates and polyethoxycarboxylates.

In an embodiment of the presently claimed invention, the cationic surfactant is selected from the group consisting of quaternized ammonium compounds, alkyl sulfates, and pyridine and imidazoline derivatives.

In an embodiment of the presently claimed invention, the quaternized ammonium compounds are polyquaternium polymers which are widely known as "PQ" polymers that comprise a quaternium ammonium moiety, and many such polymers are known in the prior art for a person skilled in the related art. For example, PQ-1 to PQ-47 polymers are duly listed in the Official Journal of the European Union, Commission Decision dated 9 Feb. 2006, 2006/257/EC. Other quaternary ammonium compounds are listed in the CTFA Cosmetic Ingredient Handbook, First Edition, on pages 41-42, incorporated herein by reference, and are described in the "History of Polymers in Haircare," Cosmetics and Toiletries, 103 (1988), incorporated herein by reference In an embodiment of the presently claimed invention, the amphoteric surfactant is selected from the group consisting of alkylbetaines, alkylamidopropylbetaines, alkylsulfobetaines, alkyl glycinates, alkyl carboxyglycinates, alkyl amphoacetates or propionates and alkyl amphodiacetates or dipropionates.

In an embodiment of the presently claimed invention, the non-ionic surfactant is selected from the group consisting of fatty alcohol polyoxyalkylene esters, alkyl polyoxyalkylene ethers which are derived from C1-C6-alcohols or from C7-C30-fatty alcohols, alkylaryl alcohol polyoxyethylene ethers, alkoxylated animal and/or plant fats and/or oils, glycerol esters, alkylphenol alkoxylates, fatty amine alkoxylates, fatty acid amide and fatty acid diethanolamide alkoxylates, ethoxylates thereof, sugar surfactants, sorbitol esters, polyoxyethylene sorbitan fatty acid esters, alkyl polyglycosides, N-alkylgluconamides, alkyl methyl sulfoxides and alkyl dimethyl phosphine oxides.

In an embodiment of the presently claimed invention, the surfactant is present in an amount in the range of ≥10.0% to ≤50.0% by weight, based on the total weight of the hair care composition.

In an embodiment of the presently claimed invention, the at least one cosmetically acceptable additive is hair conditioning agent which are suitable for topical application to the hair. The preferred conditioning agent for the hair conditioner-based composition is well known to a person skilled in the relevant field. An extensive discussion on conditioning agents may be found in "Conditioning Agents for Skin and Hair", Cosmetic Science and Technology Series, Volume 21, 1999, Marcel Dekker Publishers. The contents of the book are hereby incorporated in its entirety by reference.

In an embodiment of the presently claimed invention, the conditioning agent can be a protein or hydrolyzed cationic or non-cationic protein. Examples of these compounds include hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain. Ceramide type of compound include a ceramide, a glycoceramide, a pseudoceramide, or a neoceramide. Possible ceramide type compounds useful herein include 2-N-linoleoyl amino-octadecane-1,3-diol, 2-N-oleoyl amino-octadecane-1,3-diol, 2-N-palmitoyl amino-octadecane-1,3-diol, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N(2-hydroxy ethyl)-N-(3-cetoxyl-2-hydroxy propyl) amide of cetylic acid, N-docosanoyl N-methyl-D-glucamine and mixtures of such compounds.

In yet another embodiment of the present invention, the other types of conditioning agents can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counterion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the resin described above reduces static and enhances combing of hair in the dry state. The resin also enhances the deposition of the quaternary ammonium compound onto the hair substrate thus enhancing the conditioning effect of hair.

In yet another embodiment of the presently claimed invention, the conditioning agent can be any fatty amine known to be useful as a conditioning agent; e.g. dodecyl, cetyl or stearyl amines, such as stearamidopropyl dimethylamine.

In a further embodiment of the presently claimed invention, the conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic ester acids including mono-, di-, tri- and tetra-carboxylic acids.

In an embodiment of the presently claimed invention, the emulsifiers are selected from the group consisting of condensation products of aliphatic (C8 to C40) primary or secondary linear or branched-chain alcohols or phenols with alkylene oxides, C6-C100 ethylene oxide (EO), glycol distearate, sorbitan trioleate, propylene glycol isostearate, glycol stearate, sorbitan sesquioleate, glyceryl stearate, lecithin, sorbitan oleate, sorbitan monostearate NF, sorbitan stearate, sorbitan isostearate, steareth-2, oleth-2, glyceryl laurate, ceteth-2, PEG-30 dipolyhydroxystearate, glyceryl stearate SE, sorbitan stearate, sucrose cocoate, PEG-4 dilaurate, methyl glucose sesquistearate, PEG-8 dioleate, sorbitan laurate, PEG-40 sorbitan peroleate, laureth-4, PEG-7 glyceryl cocoate, PEG-20 almond glycerides, PEG-25 hydrogenated castor oil, stearamide MEA, glyceryl stearate, PEG-100 stearate, polysorbate 85, PEG-7 olivate, cetearyl glucoside, PEG-8 oleate, poly glyceryl-3 methylglucose distearate, Oleth-10, Oleth-10/polyoxyl 10 oleyl ether NF, ceteth-10, PEG-8 laurate, cocamide MEA, polysorbate 60 NF, polysorbate 60, polysorbate 80, isosteareth-20, PEG-60 almond glycerides, polysorbate 80 NF, PEG-20 methyl glucose sesquistearate, ceteareth-20, oleth-20, steareth-20, steareth-21, ceteth-20, isoceteth-20, polysorbate 20, polysorbate 20 NF, laureth-23, PEG-100 stearate, steareth-100, PEG-80 sorbitan laurate alone or in combinations thereof.

In an embodiment of the presently claimed invention, the conditioning agent is protein or hydrolyzed cationic or non-cationic protein, cationic surfactant such as a salt of a primary, secondary, or tertiary fatty amine, a quaternary ammonium salt, a derivative of imidazoline, or an amine oxide, fatty amine, fatly acid or derivatives, quaternary ammonium compounds, cationic polymers, natural or synthetic oils.

In yet another embodiment of the presently claimed invention, the conditioning agent is the cationic polymer which is selected from cationic guars, cationic hydroxylethyl cellulose, diallyl dimethylammonium chloride (DADMAC)-acrylamide copolymer and (3-acrylamidopropyl) trimethyl-ammonium chloride.

In a further embodiment of the presently claimed invention, the conditioning agent is natural or synthetic oil is selected from the group consisting of glycerol esters of fatty acids, linear or branched, symmetric or asymmetric dialkyl ethers having 6 to 22 carbon atoms per alkyl group and alkyl glucosides, polyethylene glycol alkyl ethers having 6 to 22 carbon atoms per alkyl group, polyethylene glycol alkyl glycerides having 6 to 22 carbon atoms per alkyl group.

In an embodiment of the presently claimed invention, the conditioning agent is present in an amount of 0.1% to 1.0% by weight, based on the total weight of the hair care composition.

In an embodiment of the present invention, suitable silicones for preparing hair styling compositions could be used along with the liquid crystal particles of the present application may be used. The preferred silicone may be selected from the group consisting of but not limiting to polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxanes, organo-modified silicone, amino functional silicones. The silicones may be used in the form of emulsions, nano-emulsions, or micro-emulsions. Further, the possible other silicones that are disclosed in WO2013064596A1 is considered for the purposes of the application and is enclosed here in its entirety.

In an embodiment of the present invention, the hair care compositions may also comprise thickeners and/or viscosifiers from the following commercial products: Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurf™ cetyl modified hydroxyethylcellulose, N-Hance™ cationic guar, N-Hance™ HP Series hydroxypropyl guar, N-Hance™ SP-100 conditioning polymer, and Supercol™ guar gum.

In an embodiment of the present invention, the hair care composition may also comprise thickeners and/or viscosifiers from the following commercial products namely Carbopol® Polymers, Fixate™ PLUS Polymer, Glucamate™ Thickeners, Amidex™ Surfactants, Chembetaine™ Surfactants, Chemoxide™ Surfactants, Chemonic™ Surfactants, Chemccinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid Diethanolamides from The Lubrizol Corporation. Salcare® and Luvigel® from BASF Corporation.

Aculyn™ 22, Aculyn™ 28, Aculyn™ 33, Aculyn™ 38, and Aculyn™ 44 from The Dow Chemical Company.

Ammonyx®C and Stepan-Mild®GCC from Stepan Company.

Stabileze®, Rapithix®A-60, Rapithix®A-100, Ultrathix®P-100, Lubrajel® and FlexiThix from ASI.

Also suitable as a thickener/rheology modifier are lightly to moderately crosslinked polyvinylpyrrolidones. Disclosures of these polymers are provided in the following patents and publications, each of which is hereby incorporated in its entirety by reference: U.S. Pat. Nos. 5,073,614; 5,312,619; 5,139,770; 5,716,634; 5,470,884; 5,759,524; 5,997,887; 6,024,942; and WIPO PCT publication numbers PCT/US10/26973, PCT/US 10/26976, PCT/US 10/26940, PCT/US 11/32993, and PCT/US 11/34515.

In an embodiment of the present invention, the at least one cosmetically acceptable additive is one or more thickening polymers. The non-limiting examples of suitable thickening polymers include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *Arachis hypogaea* (peanut) flour; ascorbyl methylsilanol pectinate; astragalus gummifer gum; attapulgite; *Avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxy sultaine; cocobetaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked bacillus/glucose/sodium glutamate ferment; cyamopsis tetragonoloba (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxy aluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatine; gellan gum; glyceryl alginate; glycine soya (soybean) flour; guar hydroxypropyltrimonium chloride; hectorite; hyaluronic acid; hydrated silica; hydrogenated potato starch; hydrogenated tallow; hydrogenated tallow amide DEA; hydrogenated tallow betaine; hydroxybutyl methylcellulose; hydroxyethyl acrylate/sodium acryloyl dimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxy stearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; minkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynol hydroxyethylcellulose; oat amide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; oliveamide DEA; oliveamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MI-PA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/™MG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/™MG copolymer; PEG-150 pentaerythrityl tetrastearate; PEG-4 rapeseedamide; PEG-150/stearyl alcohol/SMDI copolymer; phaseolus angularis seed powder; polianthes tuberosa extract; polyacrylate-3; polyacrylic acid; polycyclopentadiene; polyether-1; polyethylene/isopropyl maleate/MA copolyol; poly glyceryl-3 disiloxane dimethicone; poly glyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; pyrus cydonia seed; pyrus malus (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; rosa multiflora flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *Solanum tuberosum* (potato) starch; soyamide DEA; soyamidopropyl betaine; starch/acrylates/acrylamide copolymer; starch hydroxypropyltrimonium chloride;

stearamide AMP; stearamide DEA; stearamide DEA-distearate; stearamide DIBA-stearate; stearamide MEA;

stearamide MEA-stearate; stearamide MIPA; stearamidopropyl betaine; steareth-60 cetyl ether; steareth-100/PEG-136/HDI copolymer; stearyl alcohol; stearyl betaine; sterculia urens gum; synthetic fluorphlogopite; tall amide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *Triticum vulgare* (wheat) germ powder; *Triticum vulgare* (wheat) kernel flour; *Triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *Zea mays* (corn) starch; and blends thereof.

In an embodiment of the presently claimed invention, the thickener is selected from the group consisting of celluloses, xanthan gum, carrageenan, gellan gum, crosslinked polyacrylic acid polymers, hydrophobically modified crosslinked polyacrylic acid polymers, alkali swellable crosslinked polyacrylic acid polymers, polyethylene glycol dialkanoates, polypropylene glycol trialkyl trialkenoates.

In an embodiment of the presently claimed invention, the thickener is present in an amount in the range of ≥0.5% to ≤4.0% by weight, based on the total weight of the hair care composition.

In an embodiment of the presently claimed invention, the hair care composition comprises preservatives selected from, but are not limited to, triazoles, imidazoles, naphthalene derivatives, benzimidazoles, morpholine derivatives, dithiocarbamates, benzisothiazoles, benzamides, boron compounds, formaldehyde donors, isothiazolones, thiocyanates, quaternary ammonium compounds, iodine derivates, phenol derivatives, Phenoxyethanol and Caprylyl Glycol microbicides, pyridines, dialkyl thiocarbamates, nitriles, parabens, alkyl parabens and salts thereof.

In an embodiment of the presently claimed invention, suitable antioxidants may be added to facilitate the enhanced shelf-life of the hair styling composition of the present application. The antioxidants that can be used include vitamins such as vitamin E, vitamin E acetate, vitamin C, vitamin A, and vitamin D, and derivatives thereof. Additional exemplary antioxidants include but are not limited to propyl, octyl and dodecyl esters of gallic acid, butylated hydroxyanisole (BHA), butylated hydroxytoluene (BHT), and nordihydroguaiaretic acid.

In yet another embodiment of the presently claimed invention, the preferred fatty substance-based excipient for formulating desired hair care composition of the present application would include fatty alcohols, natural and synthetic waxes, ceramides, mineral oils, vegetable oils, animal oils, synthetic oils. In another embodiment, the other preferred fatty substance are isododecane, hydrogenated polyisobutene, squalane, isononyl isononanoate, cyclotetra- and -pentadimethicones, phenyltrimethicone, ethylene homopolymers, ethoxylated fats and oils, fluoroalkanes, seracite, shea butter, arachidyl propionate alone or in combination. For the definition of waxes, mention may be made, for example, of P. D. Dorgan, Drug and Cosmetic Industry, December 1983, pp. 30-33.

In another embodiment of the presently claimed invention, the moisturizers or humectants include glycols, glycerols, propylene glycol, diethylene glycol monoethyl ether, sorbitol, sodium salt of pyroglutamic acid, glycerol, glycerol derivatives, glycerin, Trehalose, sorbitol, maltitol, dipropylene glycol, 1,3-butylene glycol, sodium hyaluronate, and the like. Further, it is known that moisturizers that binds well with water, thereby retaining it on the hair surface are called humectants. Examples of humectants which can be incorporated into a product of the present application are glycerine, propylene glycol, polypropylene glycol, polyethylene glycol, lactic acid, sodium lactate, pyrrolidone carboxylic acid, urea, phospholipids, collagen, elastin, ceramides, lecithin sorbitol, PEG-4, and mixtures thereof. Additional suitable moisturizers are polymeric moisturizers that belong to water soluble and/or water swellable in nature. Polysaccharides such as hyaluronic acid, chitosan can also be employed along with moisturizers of the present application as binder to enhance their property.

In another embodiment of the presently claimed invention, the anti-dandruff agents that can be used are climbazole, octopirox and zinc pyrithione, salicylic acid, elemental sulfur, selenium dioxide, and the azole antimycotics.

In a further embodiment of the presently claimed invention, the hair care composition may include at least one organic UV filters which can filter out UV rays. The filter can be selected from hydro soluble or liposoluble filters, whether siliconated or non-siliconated, and mineral oxide particles, the surface of which may be treated. Hydro soluble organic UV filters can be chosen from para-amino benzoic acid and its salts, anthranilic acid and its salts, salicylic acid and its salts, hydroxy cinnamic acid and its salts, sulfonic derivatives of benzothiazoles, benzimidazoles, benzoxazoles and their salts, sulfonic derivatives of benzophenone and their salts, sulfonic derivatives of benzylidene camphor and their salts, derivatives of benzylidene camphor substituted by a quaternary amine and their salts, derivatives of phthalydene-camphosulfonic acids and their salts, sulfonic derivatives of benzotriazole, and mixtures thereof.

Suitable liposoluble organic UV filters include, but not limited to, derivatives of para-aminobenzoic acid, such as the esters or amides of para-aminobenzoic acid; derivatives of salicylic acid; derivatives of benzophenone; derivatives of dibenzoyl methane; derivatives of diphenyl acrylates; derivatives of benzofurans; UV filter polymers containing one or more silico-organic residues; esters of cinnamic acid; derivatives of camphor; derivatives of trianilino-s-triazine; the ethylic ester urocanic acid; benzotriazoles; derivatives of hydroxy phenyl triazine; Ws-resorcinol-dialkyl amino triazine; and mixtures thereof.

In a further embodiment of the presently claimed invention, the hair care composition includes coloring agents, colorants or dyes used herein include natural foods colors and dyes suitable for food, drug and cosmetic applications. These colorants are also known as FD & C, and D&C dyes and lakes and are preferably water-soluble in nature. A full recitation of all FD&C and D&C dyes and their corresponding chemical structures may be found in the Kirk-Othmer Encyclopedia of Chemical Technology, Volume 5, pages 857-884, which text is accordingly incorporated herein by reference. These coloring agents may be incorporated in amount up to about 3%, more particularly up to about 2%, and in some cases less than about 1% by weight of the personal care compositions.

In yet another embodiment of the presently claimed invention, the hair care composition comprises sequestering agent or chelating agent. The term “sequestering agent” or “chelating agent” as used herein relates to a compound which is capable of bonding or complexing a metal ion between two or more atoms of the compound, thereby neutralizing or controlling harmful effects of such metal ions, wherein holding or bonding of a metal ion is through combination of one or more different types of bonds including coordination and/or ionic bonds. The suitable organic or inorganic sequestering or chelating for the purposes of the present application is selected from the group comprising polyols, gluconates, sorbitals, mannitols, carbonates, hydroxamates, catechols, amino carboxylates, alkanolamines, metal-ion sequestrants, hydroxy-carboxylic acids, aminocarboxylic acids, amino polycarboxylic acids, polyamines, polyphosphates, phosphonic acids, crown ethers, amino acids, polycarboxylic acids, cyclodextrin, phosphonates, polyacrylates or polymeric polycarboxylates, condensed phosphates. Further, the information on sequestering and chelating agents is disclosed in T. E. Furia, CRC Handbook of Food Additives, 2nd Edition, pp. 271-294 (1972), and M. S. Peterson and A. M. Johnson (Eds.), Encyclopedia of Food Science, pp. 694-699 (1978) are incorporated herein by reference in its entirety.

In a further embodiment of the presently claimed invention, the hair care composition includes a perfume or fragrance obtained from natural or synthetic source. The fragrance may be used along with a suitable solvent, diluents or carrier. Fragrances may be added in any conventionally known method, for example, admixing to a composition or blending with other ingredients used to form a composition, in amounts which are found to be useful to increase or impart the desired scent characteristics to the disinfectant or cleaning compositions. Fragrances for the present application can be one or more selected from the following non-limiting group of compounds such as essential oils, absolutes, resinoids, resins, concretes, hydrocarbons, alcohols, aldehydes, ketones, ethers, acids, esters, acetals, ketals, nitriles, including saturated and unsaturated compounds and aliphatic, carbocyclic and heterocyclic compounds.

In an embodiment of the presently claimed invention, the hair care composition is present in the form of a rinse-off composition or leave-in composition.

In an embodiment of the presently claimed invention, the hair care composition is a rinse-off composition selected from shampoos, conditioners, hair straighteners, permanent wave and hair colours.

In yet another embodiment of the presently claimed invention, the hair care composition the leave-in composition is selected from a mousse, a hair lacquer, a hair gel, a hair lotion, a hair wax, a styling cream, a pomade, a tonic, a hair spray, a working spray, a finishing spray, a blow-dry protectant spray, a flat-iron spray, a thermal protectant spray, and a curl-enhancing spray.

In an embodiment of the presently claimed invention, the hair care composition does not include silicones In an embodiment of the presently claimed invention, the hair care composition comprises ≥1.0% to ≤15.0% by weight of at least one liquid crystal lipid particle, ≥10.0% to ≤50.0% by weight of at least one surfactant, ≥0.1% to ≤1.0% by weight of at least one conditioning agent, ≥0.5% to ≤4.0% by weight of at least one thickener, ≥50.0% to ≤90.0% by weight water, each based on the total weight of the hair care composition.

Advantages

1) The liquid crystal particle containing composition are comparable to the silicone containing hair care composition and thus can be considered as a replacement for silicone as silicone is considered to be harmful to the environment.

2) A sustainable alternative to silicone containing hair care product.

3) The process for making the liquid crystal particles is cost effective and thus sustainable for any commercial applications.

EMBODIMENTS

1. A method for conditioning of hair comprising applying to the hair at least one liquid crystal lipid particle, wherein the liquid crystal lipid particle comprises at least one compound of formula (I)

general formula (I)

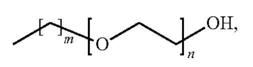

wherein m is an in the range from ≥10 to ≤24 and n is an integer in the range from ≤1 to ≥25, at least one compound of formula (II)

general formula (II)

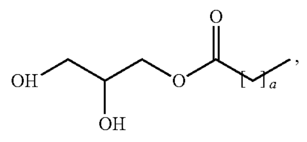

wherein a is an in the range from ≥10 to ≤24, at least one compound of formula (III)

general formula (III)

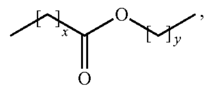

wherein x is an in the range from ≥10 to ≤24 and y is an integer in the range from ≥10 to ≤25, at least one compound of formula (IV)

general formula (IV)

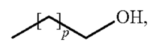

wherein p is an in the range from ≥10 to ≤16, at least one compound of formula (V)

general formula (V)

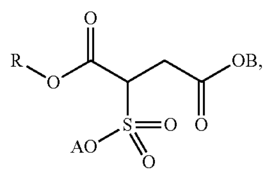

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

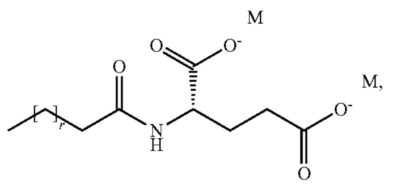

wherein r is an in the range from ≥9 to ≤18, and M is a hydrogen atom, an alkali earth metal or an alkaline earth metal.

2. Use of at least one liquid crystal lipid particle for conditioning of the hair, wherein the liquid crystal lipid particle comprises at least one compound of formula (I)

general formula (I)

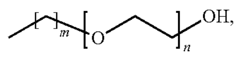

wherein m is an in the range from ≥10 to ≤24 and n is an integer in the range from to 25, at least one compound of formula (II)

general formula (II)

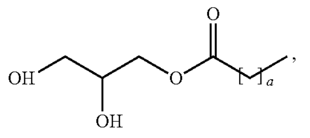

wherein a is an in the range from ≥10 to ≤24, at least one compound of formula (III)

general formula (III)

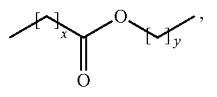

wherein x is an in the range from ≥10 to ≤24 and y is an integer in the range from ≥10 to ≤25, at least one compound of formula (IV)

general formula (IV)

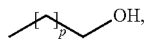

wherein p is an in the range from ≥10 to ≤16, at least one compound of formula (V)

general formula (V)

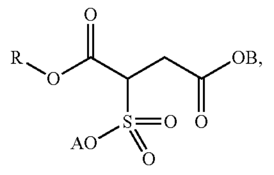

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

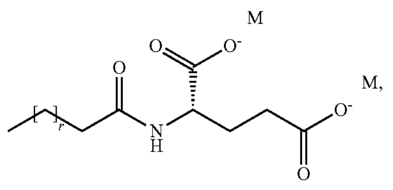

wherein r is an in the range from ≥9 to ≤18, and M is a hydrogen atom, an alkali earth metal or an alkaline earth metal.

3. The method or use according to embodiment 1 or 2, wherein the liquid crystal lipid particles have a lamellar structure with orthorhombic lateral packing.

4. The method or use according to embodiment 1 or 2, wherein the liquid crystal lipid particles have an average particle size in the range of 20 nm to 300 nm, determined using dynamic light scattering using Malvern DLS ZS90.

5. The method or use according to embodiment 1 or 2, wherein the liquid crystal lipid particles have a zeta potential is more than 20 mV when measured at 40° C., determined using Zetasizer nano ZS90.

6. The method or use according to embodiments 1 to 5, wherein the at least one compound of general formula (I) is selected from the group consisting of ceteareths, polyoxyethylene stearyl ether, and polyoxyethylene cetyl ether.

7. The method or use according to embodiments 1 to 6, wherein the at least one compound of general formula (II) is selected from the group consisting of glycerol stearate, glycerol laurate and glycerol palmitate.

8. The method or use according to embodiments 1 to 7, wherein the at least one compound of general formula (III) is selected from the group consisting of cetyl palmitate, myristyl myristate, tetra decyl tetra decanoate, and behenyl behenate.

9. The method or use according to embodiments 1 to 8, wherein the at least one compound of general formula (IV) is selected from the group consisting of lauryl alcohol, tridecyl alcohol, myristyl alcohol, pentadecyl alcohol, cetyl alcohol, palmitoleyl alcohol, heptadecyl alcohol, stearyl alcohol or mixtures thereof.

10. The method or use according to embodiments 1 to 9, wherein the at least one compound of general formula (V) is disodium $C_{10}$-$C_{18}$ alkyl sulfosuccinate.

11. The method or use according to embodiments 1 to 10, wherein the at least one compound of general formula (VI) is selected from the group consisting of sodium lauroyl glutamate, sodium cocoyl glutamate, sodium myristoyl glutamate and sodium stearoyl glutamate.

12. The method or use according to one or more of embodiments 1 to 11, wherein the liquid crystal lipid particles comprise ceteareths, glycerol stearate, cetyl palmitate, cetyl alcohol and stearyl alcohol.

13. The method or use according to embodiments 1 to 11, wherein the liquid crystal lipid particles comprise ceteareths, glycerol stearate, cetyl palmitate, myristyl myristate, cetyl alcohol and stearyl alcohol.

14. The method or use according to embodiments 1 to 11, wherein the liquid crystal lipid particles comprise ceteareths, glycerol stearate, cetyl palmitate, myristyl myristate, cetyl alcohol, stearyl alcohol and a compound selected from the group of disodium $C_{10}$-$C_{18}$ alkyl sulfosuccinate and sodium stearoyl glutamate.

15. The method or use according to embodiments 1 to 11, wherein the liquid crystal lipid particles comprise ceteareth-20, ceteareth-12, glycerol stearate, cetyl palmitate, myristyl myristate, cetyl alcohol, stearyl alcohol and a compound selected from the group of disodium $C_{16}$-$C_{18}$ alkyl sulfosuccinate and sodium stearoyl glutamate.

16. A hair care composition comprising,
 at least one liquid crystal particle as defined in one or more of embodiments 1 to 15,
 at least one cosmetically acceptable additive and water.

17. The hair care composition according to embodiment 16, wherein the at least one liquid crystal lipid particle is present in an amount in the range of ≥1.0% to ≤15.0% by weight, based on the total weight of the hair care composition 18. The hair care composition according to any of embodiments 16 to 17, wherein the at least one cosmetically acceptable additive is selected from the group consisting of thickeners, viscosity modifiers, surfactants, emulsifiers, perfumes, preservatives, UV protectants, chelating agents, cleansing agents, wetting agents, hair conditioning agents, flexibility enhancers, split modifiers, humectants, propellants, compressed gases, shine enhancers, neutralizing agents, texturizing agents, water-proofing agents, solubilizers, suspension agents, cosmetically active ingredients, hair polymers, light protection agents, bleaches, gel formers, colorants, tinting agents, tanning agents, dyes, pigments, bodying agents, moisturizers, antioxidants, defoamers, antistatics, emollients, softeners, anti-dandruff agents, hair growth agents, anti-inflammatory agents, anti-microbial agents, foam stabilizers, rheology modifiers, water softening agents, hydrotropes, buffers.

19. The hair care composition according to embodiment 18, wherein the cosmetically acceptable additive is a surfactant 20. The hair care composition according to embodiment 19, wherein the surfactant is selected from the group consisting of anionic surfactant, cationic surfactant, amphoteric surfactant and non-ionic surfactant.

21. The hair care composition according to embodiment 20, wherein the hair care composition comprises at least one anionic surfactant and at least one amphoteric surfactant.

22. The hair care composition according to embodiment 21, wherein the surfactant is an anionic surfactant.

23. The hair care composition according to embodiment 22, wherein the anionic surfactant is selected from the group consisting of alkyl sulfates, alkyl ether sulfates, alkylester sulfonates, alkylbenzene sulfonates, primary or secondary alkylsulfonates, alkylglycerol sulfonates, sulfonated polycarboxylic acids, sulfates of alkylglycosides, sulfated alkyl amides, alkylphosphates, the salts of saturated or unsaturated fatty acids, polyoxyalkylene ether acetate, paraffin sulfonates, N-acyl N-alkyltaurates, isethionates, alkylsuccinamates, N-acyl sarcosinates, alkylsulfosuccinates, monoesters or diesters of sulfosuccinates and polyethoxycarboxylates.

24. The hair care composition according to embodiment 20, wherein the surfactant is a cationic surfactant.

25. The hair care composition according to embodiment 24, wherein the cationic surfactant is selected from the group consisting of quaternized ammonium compounds, alkyl sulfates, and pyridine and imidazoline derivatives.

26. The hair care composition according to embodiments 20 or 21, wherein the surfactant is an amphoteric surfactant.

27. The hair care composition according to embodiment 26, wherein the amphoteric surfactant is selected from the group consisting of alkylbetaines, alkylamidopropylbetaines, alkylsulfobetaines, alkyl glycinates, alkyl carboxyglycinates, alkyl amphoacetates or propionates and alkyl amphodiacetates or dipropionates.

28. The hair care composition according to embodiment 20, wherein the surfactant is a non-ionic surfactant.

29. The hair care composition according to embodiment 28, wherein the non-ionic surfactant is selected from the group consisting of fatty alcohol polyoxyalkylene esters, alkyl polyoxyalkylene ethers which are derived from C1-C6-alcohols or from C7-C30-fatty alcohols, alkylaryl alcohol polyoxyethylene ethers, alkoxylated animal and/or plant fats and/or oils, glycerol esters, alkylphenol alkoxylates, fatty amine alkoxylates, fatty acid amide and fatty acid diethanolamide alkoxylates, ethoxylates thereof, sugar surfactants, sorbitol esters, polyoxyethylene sorbitan fatty acid esters, alkyl polyglycosides, N-alkylgluconamides, alkyl methyl sulfoxides and alkyl dimethyl phosphine oxides.

30. The hair care composition according any of the embodiments 16 to 29, wherein the at least one surfactant is present in an amount in the range of ≥10.0% to ≤50.0% by weight, based on the total weight of the hair care composition.

31. The hair care composition according to embodiment 18, wherein the at least one cosmetically acceptable agent is a hair conditioning agent.

32. The hair care composition according to embodiment 31, wherein the at least one conditioning agent selected form the group consisting of protein or hydrolyzed cationic or non-cationic protein, cationic surfactant such as a salt of a primary. secondary, or tertiary fatty amine, a quaternary ammonium salt, a derivative of imadazoline, or an amine oxide, fatty amine, fatly acid or derivatives, quaternary ammonium compounds, cationic polymers, natural or synthetic oils.

33. The hair care composition according to embodiment 32, wherein the cationic polymers are selected from cationic guars, cationic hydroxylethyl cellulose, diallyl dimethylammonium chloride (DADMAC)-acrylamide copolymer and (3-acrylamidopropyl) trimethyl-ammonium chloride.

34. The hair care composition according to embodiment 32, wherein the natural or synthetic oil is selected from the group consisting of glycerol esters of fatty acids, linear or branched, symmetric or asymmetric dialkyl ethers having 6 to 22 carbon atoms per alkyl group and alkyl glucosides, polyethylene glycol alkyl ethers having 6 to 22 carbon atoms per alkyl group, polyethylene glycol alkyl glycerides having 6 to 22 carbon atoms per alkyl group.

35. The hair care composition according to any of embodiments 31 to 34, wherein the at least one conditioning agent is present in an amount in the range of 0.1% to 1.0% by weight, based on the total weight of the hair care composition.

36. The hair care composition according to embodiment 18, wherein the at least one cosmetically acceptable agent is a thickener.
37. The hair care composition according to embodiment 36, wherein the at least one thickener is selected from the group consisting of celluloses, xanthan gum, carrageenan, gellan gum, crosslinked polyacrylic acid polymers, hydrophobically modified crosslinked polyacrylic acid polymers, alkali swellable crosslinked polyacrylic acid polymers, polyethylene glycol dialkanoates, polypropylene glycol trialkyl triakenoate.
38. The hair care composition according to embodiments 36 or 37, wherein the at least one thickener is present in an amount in the range of ≥0.5% to ≤4.0% by weight, based on the total weight of the hair care composition.
39. The hair care composition according to any of embodiments 16 to 38, comprising
    ≥1.0% to ≤15.0% by weight of at least one liquid crystal particle,
    ≥10.0% to ≤50.0% by weight of at least one surfactant,
    ≥0.1% to ≤1.0% by weight of at least one conditioning agent,
    ≥0.5% to ≤4.0% by weight of at least one thickener,
    ≥50.0% to ≤90.0% by weight water,
    each based on the total weight of the hair care composition.
40. The hair care composition according to any of embodiments 16 to 39, wherein the hair care composition is present in the form of a rinse-off composition or leave-in composition.
41. The hair care composition according to embodiment 40, wherein the rinse-off composition is selected from shampoos, conditioners, hair straighteners, permanent wave and hair colours.
42. The hair care composition according to embodiment 40, wherein the leave-in composition is selected from a mousse, a hair lacquer, a hair gel, a hair lotion, a hair wax, a styling cream, a pomade, a tonic, a hair spray, a working spray, a finishing spray, a blow-dry protectant spray, a flat-iron spray, a thermal protectant spray, and a curl-enhancing spray.
43. A method for conditioning of hair comprising applying to the hair the composition according to any of embodiments 16 to 42.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the presently claimed invention, which are apparent to one skilled in the art.

Materials:

Materials from BASF:

Emulgade® SE-PF is glyceryl stearate, ceteareth-20, ceteareth-12, cetyl alcohol, cetyl palmitate is an emulsifying base.

Eumulgin® B1 is ceteareth-12 (cetyl stearyl alcohol with 12 mol EO) which is a non-ionic emulsifier Cetiol®MM is myristyl myristate which is an emollient Eumulgin® Prisma is disodium C16-C18 alkyl sulfosuccinate which is an anionic emulsifier Eumulgin®SG is sodium steaoryl glutamate which is an anionic emulsifier.

Texapon® NSO UP is sodium laureth sulfate (Sodium C12-14 ether sulfate+2 EO), which is an anionic surfactant.

Texapon® SFA

Dehyton® PK 45 is cocamidopropyl betaine which is an amphoteric surfactant.

Plantapon® LGC sorb is sodium lauryl glucose carboxylate (and) lauryl glucoside which is an anionic surfactant.

Plantapon® AGC HC is sodium cocoyl glutamate which is a co-surfactant.

Plantacare® 2000 UP is decyl glucoside which is a nonionic surfactant

Plantacare® 818 UP is coco-glucoside which is a nonionic surfactant.

Plantasil®Micro is blended dicaprylyl ether (and) decyl glucoside (and) glyceryl oleate is a hair care additive.

Comperlan® 100C is cocamide MEA which is a thickener.

Euperlan® PK710Benz is glycol distearate (and) sodium laureth sulfate (and) cocamide MEA which is pearl shine concentrate.

Material from DOW

Xiameter® MEM1352 emulsion is a 60% non-ionic emulsion of a blend of ultra-high molecular weight polydimethylsiloxane and high molecular weight polydimethylsiloxane.

PQ10 is polyquaternium 10

Methods:

Measurement of particle size: Particle size measurement of the liquid crystal lipid particles was done using Malvern DLS Z590.

Measurement of zeta potential: Zeta potential was measured using Zetasizer nano ZS90 (Malvern)

Example 1

Base Composition of the Liquid Crystal Lipid Particles (Nanowax)

TABLE 1

| Part | Ingredient | Ex. 1 (% w/w) |
|---|---|---|
| A | Emulgade ® SE-PF | 7.50 |
| | Eumulgin ® B1 | 7.50 |
| | Cetiol ® MM | 15.00 |
| B | Water | 28.80 |
| | Eumulgin ® SG | 0.20 |
| C | Water | 10.00 |
| | Glycerin | 20.00 |
| D | Water | 10.00 |
| | preservative | q.s. |

q.s. = quantity sufficient

Nanowax

Process of manufacture: Phase inversion temperature emulsification method

1. Heat up part A and B to 85° C., and pre-dissolve part C at 25 C.
2. Mix part A for 3 min.
3. Add part B into part A with homogenizing at 85° C.
4. Cool down the base to 70-75° C. with homogenizing until the appearance of base is changed from milky white to semi-transparent.

5. Add part C into the base and homogenize for 1 min.
6. Cool down the base to 28° C.

Macrowax

The process for preparing macrowax is the same as the process for preparing nanowax except the temperature is 65° C.

Example 2

Compatibility of the Surfactant with Liquid Crystal Lipid Particles

Various surfactants were evaluated for their compatibility with the liquid crystal lipid particles by evaluating the formulation of the surfactant with liquid crystal lipid particles for 1 month at room temperature, 4° C. and −20° C.

The formulations were prepared based on the below table. The formulation was kept at different temperatures, namely room temperature, 4° C. and −20° C. for 1 month. After 1 month the formulations were checked for the appearance. Specifically, the formulations were checked if they were transparent or hazy. It is desired that the formulations remain transparent on storage.

Process:

1) Mix water and PQ 10 under stirring until polymer disperse to uniform at room temperature.
2) add surfactant into phase A under stirring until uniform.
3) Add phase C one by one under stirring until transparent.

TABLE 2

| | Ingredient | Ex. 2 (wt %) | Ex. 3 (wt %) | Ex. 4 (wt %) | Ex. 5 (wt %) | Ex. 6 (wt %) | Ex. 7 (wt %) | Ex. 8 (wt %) | Ex. 9 (wt %) |
|---|---|---|---|---|---|---|---|---|---|
| A | Water | To 100 | To 100 | To 100 | To 100 | To 100 | To 100 | To 100 | To 100 |
| | PQ10 | 0.2 | 0.2 | 0.2 | 0.2 | 0.2 | 0.2 | 0.2 | 0.2 |
| B | Texapon ® NSO UP | 33.3 | 16.7 | | | | | | |
| | Dehyton ® PK45 | | 11.1 | 22.2 | | | | | |
| | Texapon ® SFA | | | | 33.3 | | | | |
| | Plantapon ® LGC Sorb | | | | | 33.3 | | | |
| | Plantapon ® ACG HC | | | | | | 25 | | |
| | Plantacare ® 2000UP | | | | | | | 20 | |
| | Plantacare ® 818UP | | | | | | | | 20 |
| C | Nano wax as per Ex. 1 | 4 | 4 | 4 | 4 | 4 | 4 | 4 | 4 |
| | G-Plus | 0.5 | 0.5 | 0.5 | 0.5 | 0.5 | 0.5 | 0.5 | 0.5 |

TABLE 3

Compatibility of various surfactant active with liquid crystal lipid particles

| Surfactant | RT, 1 m | 4° C., 1 m | −20° C., 1 m |
|---|---|---|---|
| Texapon ® NSO UP, Dehyton ® PK 45 | Yes | Yes | No |
| Texapon ® NSO UP | Yes | No | No |
| Texapon ® SFA | Not compatible | | |
| Dehyton ® PK 45 | Yes | Yes | Yes |
| Plantapon ® LGC sorb | Yes | Yes | No |
| Plantapon ® AGC HC | Yes | No | No |
| Plantacare ® 2000 UP | No | No | No |
| Plantacare ® 818 UP | Yes | Yes | Yes |

The surfactant actives were formulated as per table 2 and the compatibility at room temperature, 4° C. and −20° C. was evaluated after 1 month as indicated in table 3.

Thus, it can be seen that liquid crystal lipid particles are compatible with Dehyton PK 45 and Plantacare 818 UP.

Example 3

The liquid crystal nanoparticles used in hair conditioning formulation as indicated in the below table.

TABLE 4

| | NW-000 Blank | NW-1 Nanowax | NW-2 Macrowax | NW-3 Individual ingredient | NW-4 Plantasil ® Micro |
|---|---|---|---|---|---|
| PQ-10 | 0.2% | 0.2% | 0.2% | 0.2% | 0.2% |
| Texapon ® NSO UP | 33.3% | 33.3% | 33.3% | 33.3% | 33.3% |
| Dehyton ® PK 45 | 7.5% | 7.5% | 7.5% | 7.5% | 7.5% |
| Nanowax (as per ex.1) | — | 4.0% | — | — | — |
| Macrowax (as per ex.1) | — | — | 4.0% | — | — |
| Individual ingredients (Ingredients as indicated in table 1 individually mixed) | — | — | — | 4.0% | — |
| Plantasil ® Micro | — | — | — | — | 4.0% |
| Water | to 100% | to 100% | to 100% | to 100% | to 100% |

The formulations with LCLP were compared with Plantasil® Micro since it is considered to be an innovative microemulsion which provides improved hair conditioning performance to shampoos, especially suited for silicone alternative formulations.

Example 4

The formulations were compared for the combing performance on wet and dry hair using the below procedure Wet Combing:

1. Surfactant solution was used to clean the new hair strand (1 g/strand) and the strands were place it in the climate-controlled room after chemical oxidation (bleaching).
2. After soaking three hair tresses completely in the water, the wet hair was tested on the Zwick combing machine immediately (five hair tresses for each formula and use the same comb with the same formula) to get the value of Combing work before treatment.
3. The wet hair were treated with 0.25 g shampoo twice. After incubation for 5 min, the hair tresses were rinsed under the rinsing device. The hair tresses were then tested on the Zwick combing machine immediately to get the value of Combing work after treatment.
4. Residual combing work was calculated as; Residual combing work=Wet combing work after treatment/Wet combing work before treatment Dry Combing:

1. Surfactant solution was used to clean the new hair strand (2 g/strand) and the strands were place it in the climate-controlled room after chemical oxidation (bleaching).
2. The bleached dry hair were tested on the Zwick combing machine (five hair tresses for each formula and use the same comb with the same formula) to get the value of Combing work before treatment.
3. Three hair tresses were fully wetted under rinsing device and treat them with 0.5 g shampoo twice. After incubation 5 min, rinse the hair tresses under rinsing device and dry in the controlled room until equilibrium.
4. The dried hair tresses were tested on the Zwick combing machine (use the same comb with the same formula) to get the value of Combing work after treatment.
5. Residual combing work was calculated as: Calculate Residual combing work=Dry combing work after treatment/Dry combing work before treatment

TABLE 5

| Test sample | Wet combing | Dry combing |
|---|---|---|
| NW-000 Blank | 85% | 61% |
| NW-4 Plantasil ® Micro | 27% | 63% |
| NW-1 nanowax | 26% | 42% |
| NW-2 Macro wax | 30% | 76% |
| NW-3 Individual ingredients | 44% | 90% |

A lower value indicates a lower force is required for combing thus indicates better performance.

Thus, in the above table 5, a lower value for nano-sized LCLP indicates the better performance of liquid crystal lipid particles and it is also comparable to Plantasil® Micro.

Example 5

The formulation of example 3, NW1 and NW4 and were repeated with 6% of Nanowax (From example 1) and 6% of Plantasil Micro respectively and the formulations were tested for combing performance. The results of the same are indicated in the below table 6.

TABLE 6

| Test sample | | Wet combing | Dry combing |
|---|---|---|---|
| nano-sized | 4% | 26% | 42% |
| LCLP | 6% | 17% | 58% |
| Plantasil Micro | 4% | 27% | 63% |
| | 6% | 18% | 70% |

The results indicate that liquid crystal lipid particles and Plantasil® Micro are comparable.

Example 6

Silicone Deposition in the Presence and Absence of Liquid Crystal Lipid Particles

TABLE 7

| Ingredient | NW-5 | NW-6 |
|---|---|---|
| Ucare ® Polymer JR-400 | 0.2 | 0.2 |
| Texapon ® NSO UP | 33.3 | 33.3 |

TABLE 7-continued

| Ingredient | NW-5 | NW-6 |
|---|---|---|
| Dehyton ® PK 45 | 7.5 | 7.5 |
| Comperlan ® 100C | 1.0 | 1.0 |
| Xiameter MEM1352 Emulsion | 3.3 | 3.3 |
| Nanowax | — | 4.0 |
| NaCl | 0.5 | 0.5 |
| Euperlan ® PK710Benz | 2.0 | 2.0 |
| Preservative | q.s. | q.s. |
| Water | To 100 | To 100 |

Quantification of the Amount of Silicone Deposited on the Hair:

NMR-Qualitative and Quantitative Determination of Silicone OH

Materials

Deuterated chloroform with TDME (CDCl3)

NMR-tubes 5 mm

Petri dishes

Sample Preparation (Solvent Method)

1. Average 5 points per sample and mix well
2. 1 g of samples were transferred in a 250 ml bottle and mixed with 100 ml of n-Pentane
3. Shake 1 h and waited for phase separation
4. The solvent was transferred into petri dish and dried them completely at room temperature
5. The residues were dissolved in 1 ml deuterated chloroform with TDME as internal reference standard and then transferred into an NMR-tube
6. Each sample of 3 parallel, and each sample extraction 2 times

TABLE 8

| | NW-5 | NW-6 |
|---|---|---|
| Content of polydimethylsiloxane deposited on hair | 27.00 mg/kg | 232.08 mg/kg |

Thus, it can be seen that the amount of silicone deposition in cases, where Nanowax is used, is about 10 times more than in its absence, suggesting that the amount of silicone in the conditioner could be reduced but the same effect could be achieved.

The invention claimed is:

1. A method for conditioning of hair comprising applying to the hair at least one liquid crystal lipid particle, wherein the liquid crystal lipid particle comprises, at least one compound of formula (I)

general formula (I)

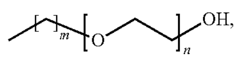

wherein m is an integer in the range from ≥10 to ≤24 and n is an integer in the range from ≥1 to ≤25, at least one compound of formula (II)

general formula (II)

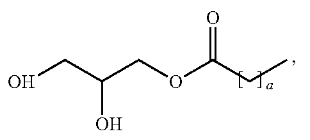

wherein a is an integer in the range from ≥10 to ≤24, at least one compound of formula (III)

general formula (III)

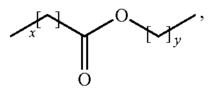

wherein x is an integer in the range from ≥10 to ≤24 and y is an integer in the range from ≥10 to ≤25, at least one compound of formula (IV)

general formula (IV)

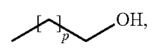

wherein p is an integer in the range from ≥10 to ≤16, at least one compound of formula (V)

general formula (V)

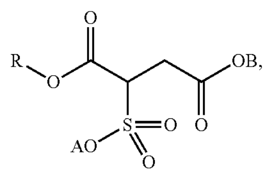

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

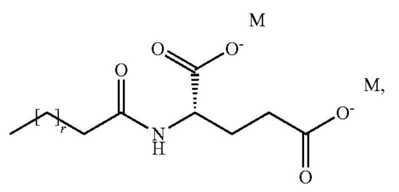

wherein r is an integer in the range from ≥9 to ≤18, and M is a hydrogen atom, an alkali earth metal or an alkaline earth metal;

wherein the at least one compound of general formula (II) is selected from the group consisting of glycerol stearate, glycerol laurate and glycerol palmitate; and wherein the liquid crystal lipid particles have an average particle size in the range of ≥20 nm to ≤300 nm, determined using dynamic light scattering using Malvern DLS ZS90.

2. The method according to claim 1, wherein the liquid crystal lipid particles have a lamellar structure with orthorhombic lateral packing.

3. The method according to claim 1, wherein the liquid crystal lipid particles have a zeta potential is more than 20 mV, when measured at 40° C., determined using Zetasizer nano ZS90.

4. The method according to claim 1, wherein the at least one compound of general formula (I) is selected from the group consisting of ceteareths, polyoxyethylene stearyl ether, and polyoxyethylene cetyl ether.

5. The method according to claim 1, wherein the at least one compound of general formula (III) is selected from the group consisting of cetyl palmitate, myristyl myristate, tetra decyl tetra decanoate, and behenyl behenate.

6. The method according to claim 1, wherein the at least one compound of general formula (IV) is selected from the group consisting of lauryl alcohol, tridecyl alcohol, myristyl alcohol, pentadecyl alcohol, cetyl alcohol, palmitoleyl alcohol, heptadecyl alcohol, stearyl alcohol or mixtures thereof.

7. The method according to claim 1, wherein the at least one compound of general formula (V) is disodium $C_{10}$-$C_{18}$ alkyl sulfosuccinate.

8. The method according to claim 1, wherein the at least one compound of general formula (VI) is selected from the group consisting of sodium lauroyl glutamate, sodium cocoyl glutamate, sodium myristoyl glutamate and sodium steraroyl glutamate.

9. The method according to claim 1, wherein the liquid crystal lipid particles comprise ceteareths, glycerol stearate, cetyl palmitate, cetyl alcohol and stearyl alcohol.

10. The method according to claim 1, wherein the liquid crystal lipid particles comprise ceteareths, glycerol stearate, cetyl palmitate, myristyl myristate, cetyl alcohol and stearyl alcohol.

11. The method according to claim 1, wherein the liquid crystal lipid particles comprise ceteareths, glycerol stearate, cetyl palmitate, myristyl myristate, cetyl alcohol, stearyl alcohol and a compound selected from the group of disodium $C_{10}$-$C_{18}$ alkyl sulfosuccinate and sodium steraroyl glutamate.

12. The method according to claim 1, wherein the liquid crystal lipid particles comprise ceteareth-20, ceteareth-12, glycerol stearate, cetyl palmitate, myristyl myristate, cetyl alcohol, stearyl alcohol and a compound selected from the group of disodium $C_{16}$-$C_{18}$ alkyl sulfosuccinate and sodium steraroyl glutamate.

13. A hair care composition comprising, at least one liquid crystal particle as defined in claim 1, at least one cosmetically acceptable additive and water.

14. The hair care composition according to claim 13, wherein the at least one liquid crystal lipid particle is present in an amount in the range of ≥1.0% to ≤15.0% by weight, based on the total weight of the hair care composition.

15. The hair care composition according to claim 13, wherein the at least one cosmetically acceptable additive is selected from the group consisting of thickeners, viscosity modifiers, surfactants, emulsifiers, perfumes, preservatives, UV protectants, chelating agents, cleansing agents, wetting agents, hair conditioning agents, flexibility enhancers, split modifiers, humectants, propellants, compressed gases, shine enhancers, neutralizing agents, texturizing agents, waterproofing agents, solubilizers, suspension agents, cosmetically active ingredients, hair polymers, light protection agents, bleaches, gel formers, colorants, tinting agents, tanning agents, dyes, pigments, bodying agents, moisturizers, antioxidants, defoamers, antistatics, emollients, softeners, anti-dandruff agents, hair growth agents, anti-inflammatory agents, anti-microbial agents, foam stabilizers, rheology modifiers, water softening agents, hydrotropes and buffers.

16. The hair care composition according to claim 15 wherein the cosmetically acceptable additive is a surfactant.

17. The hair care composition according to claim 16, wherein the surfactant is selected from the group consisting of anionic surfactant, cationic surfactant, amphoteric surfactant and non-ionic surfactant.

18. The hair care composition according to claim 16, wherein the at least one surfactant is present in an amount in the range of ≥10.0% to ≤50.0% by weight, based on the total weight of the hair care composition.

19. The hair care composition according to claim 15, wherein the at least one cosmetically acceptable agent is a hair conditioning agent.

20. The hair care composition according to claim 19, wherein the at least one conditioning agent selected form the group consisting of protein or hydrolyzed cationic or non-cationic protein, cationic surfactant such as a salt of a primary, secondary, or tertiary fatty amine, a quaternary ammonium salt, a derivative of imidazoline, or an amine oxide, fatty amine, fatty acid or derivatives, quaternary ammonium compounds, cationic polymers, natural or synthetic oils.

21. The hair care composition according to claim 19, wherein the at least one conditioning agent is present in an amount in the range of 0.1% to 1.0% by weight, based on the total weight of the hair care composition.

22. The hair care composition according to claim 15, wherein the at least one cosmetically acceptable agent is a thickener.

23. The hair care composition according to claim 22, wherein the at least one thickener is present in an amount in the range of ≥0.5% to ≤4.0% by weight, based on the total weight of the hair care composition.

24. A method for conditioning the hair comprising applying to the hair a composition according to claim 13.

25. The method for conditioning hair according to claim 1, wherein the liquid crystal lipid particles have an average particle size in the range of ≥20 nm to ≤150 nm, determined using dynamic light scattering using Malvern DLS ZS90.

26. A method for conditioning of hair comprising applying to the hair at least one liquid crystal lipid particle, wherein the liquid crystal lipid particle consists of:

at least one compound of formula (I)

general formula (I)

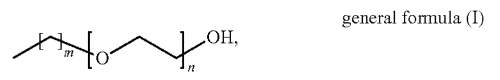

wherein m is an integer in the range from ≥10 to ≤24 and n is an integer in the range from ≥1 to ≤25, at least one compound of formula (II)

general formula (II)

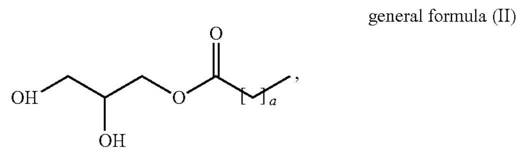

wherein a is an integer in the range from ≥10 to ≤24, at least one compound of formula (III)

general formula (III)

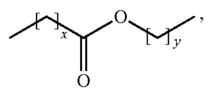

wherein x is an integer in the range from ≥10 to ≤24 and y is an integer in the range from ≥10 to ≤25, at least one compound of formula (IV)

general formula (IV)

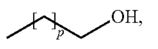

wherein p is an integer in the range from ≥10 to ≤16, at least one compound of formula (V)

general formula (V)

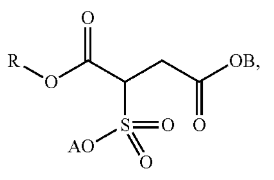

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

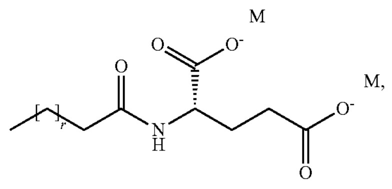

wherein r is an integer in the range from ≥9 to ≤18, and M is a hydrogen atom, an alkali earth metal or an alkaline earth metal;

wherein the at least one compound of general formula (II) is selected from the group consisting of glycerol stearate, glycerol laurate and glycerol palmitate; and wherein the liquid crystal lipid particles are in the form of a nanowax have an average particle size in the range of ≥20 nm to ≤300 nm, determined using dynamic light scattering using Malvern DLS ZS90;

and wherein the liquid crystal lipid particles are obtained by a phase inversion temperature emulsification method.

* * * * *